United States Patent [19]

Buus et al.

[11] 3,966,930

[45] June 29, 1976

[54] PHENOTHIAZINE DERIVATIVES, COMPOSITIONS THEREOF AND METHODS OF PREPARATION THEREOF

[75] Inventors: Jørn Lasse Martin Buus, Bjaeverskov; Niels Lassen, Gentofte, both of Denmark

[73] Assignee: Kefalas A/S, Copenhagen-Valby, Denmark

[22] Filed: May 30, 1974

[21] Appl. No.: 474,530

[30] Foreign Application Priority Data
June 8, 1973 United Kingdom............... 27527/73

[52] U.S. Cl............................. 424/247; 260/243 A
[51] Int. Cl.²............... C09D 279/20; C09D 279/22
[58] Field of Search.................. 260/243 A; 424/247

[56] References Cited
UNITED STATES PATENTS

| | | | |
|---|---|---|---|
| 2,921,069 | 1/1960 | Ullyot............................ | 260/243 A |
| 2,945,030 | 7/1960 | Gordon........................... | 260/243 A |
| 3,004,028 | 10/1961 | Dolliver et al.................. | 260/243 A |
| 3,047,571 | 7/1962 | Jacob et al...................... | 260/243 A |
| 3,075,976 | 1/1963 | Jacob et al...................... | 260/243 A |
| 3,169,962 | 2/1965 | Jacob et al...................... | 260/243 A |
| 3,227,708 | 1/1966 | Yale et al. ...................... | 260/243 A |

Primary Examiner—John D. Randolph
Attorney, Agent, or Firm—Gordon W. Hueschen

[57] ABSTRACT

Fluoro-substituted phenothiazine derivatives as well as their non-toxic pharmaceutically acceptable acid addition salts having pronounced neuroleptic properties and a relatively low degree of undesired side effects, a method for the preparation of said derivatives, pharmaceutical compositions containing same which may be administered to animals, including human beings, orally or parenterally.

25 Claims, No Drawings

PHENOTHIAZINE DERIVATIVES, COMPOSITIONS THEREOF AND METHODS OF PREPARATION THEREOF

BACKGROUND OF THE INVENTION

In the past, several drugs having a tricyclic structure have been found useful in the treatment of severe psychotic disorders, especially of the schizophrenic type. Most of these derivatives are phenothiazine derivatives which are substituted in the 2-position of one of the benzene rings and having at the ring nitrogen atom an alkyl side chain substituted with a tertiary amino group at a position three carbon atoms from the ring nitrogen atom. The tertiary amino group may also form part of a heterocyclic ring system and such a system, especially the piperazine ring system, is present in several very strong neuroleptic drugs. Also thiaxanthenes substituted in equivalent positions with similar groups and having an unsaturated bond have been found useful in the treatment of psychoses. It is a wellknown fact that the aforementioned mono-substituted phenothiazines or thiaxanthenes have a relatively short duration of effect. While phenothiazines having substituents in both phenyl rings may be broadly known none have been found useful so far.

SUMMARY OF THE INVENTION

According to the present invention it has now surprisingly been found that certain phenothiazine derivatives which are substituted in the 2-position with groups of the ordinary type, in the 7-position with a fluorine atom and, containing in the alkyl side chain a dimethylamino, a piperazine or piperidine group, have neuroleptic properties of the same level or stronger than the known phenothiazine-neuroleptics but maintain a much longer effect when administered to a living animal body when they are evaluated according to standard reliable published test methods.

The novel phenothiazines according to the present invention may be represented by the following general formula:

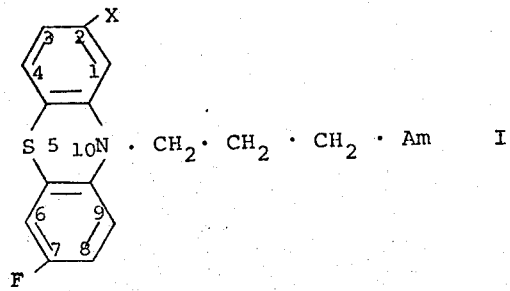

wherein "Am" is —N(CH$_3$)$_2$ or

X is —Cl, —CF$_3$, —CO · CH$_3$ or —SO$_2$·N(CH$_3$)$_2$, Y is >NH, >N·CH$_3$, >N·CH$_2$·CH$_2$OH, >N·CH$_2$·CH$_2$OAc, >CH·CH$_2$·CH$_2$OH or >CH·CH$_2$·CH$_2$OAc and —Ac is an acyl radical of an aliphatic carboxylic acid having one to seventeen carbon atoms inclusive, as well as N-oxides thereof.

Preferred compounds of this invention are those of Formula I in which X is —CF$_3$.

This invention also includes pharmaceutically acceptable salts of the above defined bases formed with nontoxic organic and inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, bis methylene-salicyclic, methanesulfonic, ethanedisulfonic, acetic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromotheophylline. Exemplary of such inorganic salts are those with hydrochloric, hydrobromic, sulfuric, sulfamic, phosphoric and nitric acids. of course, these salts may also be prepared by the classical method of double decomposition of appropriate salts which is wellknown to the art. The compounds of Formula I and the non-toxic acid additions salts thereof may be administered both orally and parenterally, for example in the form of tablets, capsules, powders, syrups or solutions for injection.

According to a feature of the present invention, the phenthiazine derivatives of general Formula I are prepared by a process which comprises reacting a phenothiazine of the general formula:

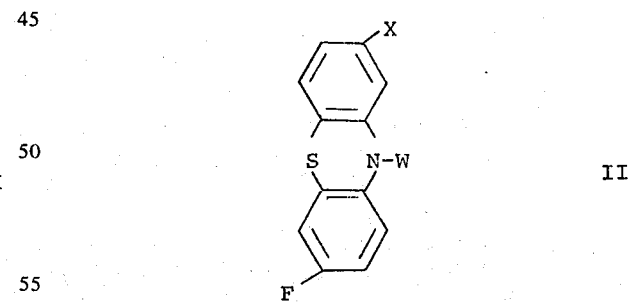

with a compound of the general formula:

wherein X and Am are as previously defined and one of the groups W and V represents a hydrogen atom and the other a group —CH$_2$·CH$_2$·CH$_2$—Z, Z representing an electronegative residue such as a halogen atom, for example chlorine or bromine, a sulphate group, for example methylsulphate, or a sulphonate group, for example toluene-p-sulphonate or methanesulphonate, whereupon possible protecting groups are removed and, if desired, reacting the compound of Formula I with hydrogen peroxide or acylating any hydroxyl group present and isolating the compound of Formula I as the free base or an acid additions salt thereof. Preferably, the symbol Z is a chlorine or bromine atom.

The reaction may be effected with or without a solvent in the presence or absence of a condensing agent.

When W represents a hydrogen atom and V represents the group —CH$_2$·CH$_2$·CH$_2$-Z, it is advantageous to use a solvent of the group of aromatic hydrocarbons (for example, toluene or xylene), ethers (for example diethyl ether) or tertiary amides (for example dimethylformamide) in the presence of a condensing agent, preferably of the class of alkali metals and their derivatives (such as for example hydrides, amides, hydroxides, alcoholates, metal alkyl or aryls) and, more particularly, metallic sodium or potassium, sodamide, powdered sodium or potassium hydroxide, lithium or sodium hydride, sodium tertbutoxide, butyllithium, phenyllithium or phenylsodium. The reaction is preferably carried out at the boiling temperature of the solvent. It is particularly advantageous to use a protecting group, such as a benzyl group, when Y is >N·CH$_2$·CH$_2$OH or >CH·CH$_2$·CH$_2$OH. The protecting group is after the reaction then split off in wellknown manner, for example by heating with concentrated hydrochloric acid or by hydrogenation.

When esterifying the compounds of Formula I wherein Y is >N·CH$_2$·CH$_2$OH or >CH·CH$_2$·CH$_2$OH the reaction is carried out in wellknown manner with acid anhydrides or acid halides in wellknown manner. The acid anhydrides or acid halides are preferably from aliphatic acids having from one to seventeen carbon atoms, for example acetic acid, propionic acid, n-butyric acid, enanthic acid, decanoic acid and palmitic acid. When preparing a N-oxide, the compound of Formula I is preferably reacted in the form of the free base with hydrogen peroxide in a lower alkanol, such as methanol, ethanol, or the like.

The starting materials of Formula II may conveniently be prepared by methods wellknown in the art for the preparation of such compounds.

It is to be understood that obvious chemical equivalents and modifications of the methods of the present invention apparent to those skilled in the art fall within the scope of the present invention.

The starting materials of formula II are novel compounds and fall within the scope of the present invention. Of the compounds of Formula I, especially those where X is —CF$_3$, have shown outstanding effects in tests on animals.

The following examples are given to illustrate the methods and products of the present invention but, they are to be understood as exemplary only and are not to be construed as limiting.

EXAMPLE 1

2-Trifluoromethyl-7-fluoro-10-(3'-(4-(2-hydroxyethyl)-piperazin-1-yl)propyl)phenothiazine and its dioxalate.

The starting material, 2-trifluoromethyl-7-fluorophenothiazine, was prepared in the following way:

54 grams of 4-fluorothiophenol were dissolved in 200 milliliters of 99% ethanol, 32 grams of 90% sodium ethylate were added and 100 grams of 1-trifluoromethyl-4-chloro-3-nitrobenzene added dropwise while the reaction temperature was kept below 20° centigrade. The reaction mixture was left standing for about 18 hours, poured into water and the resulting mixture extracted with ether-methylenechloride (1:1). The organic layer was separated and washed with 2N sodium hydroxide solution, water, dried over anhydrous magnesium sulphate and evaporated with petrol ether. Upon cooling 84 grams of 4-(4'-fluorophenylthio)-3-nitrobenzoyl-trifluoride crystallized, which melts at 64°–64° Centigrade.

60 grams of 4-(4'-fluorophenylthio)-3-nitrobenzoyl-trifluoride and 125 grams of triethyl phosphite were dissolved in 1900 milliliters of cumene and refluxed for 18 hours in an atmosphere of nitrogen. After cooling the reaction mixture was washed with water, 2N sodium hydroxide solution, 4N hydrochloric acid, aqueous ferro sulphate and water. The organic layer was separated off and evaporated to dryness at reduced pressure (1 mm Hg). The red oil which remained was distilled at 0.3 mm Hg and the fraction from 160°–200° Centigrade crystallized and was recrystallized from ether/petroleum ether (1:1). The crystals of 2-trifluoromethyl-7-fluoro-phenothiazine were sucked off and dried. They melted at 136°–137° Centigrade. Yield: 10 grams.

8 grams of 2-trifluoromethyl-7-fluorophenothiazine were dissolved in 50 milliliters of dimethylformamide and the solution added to 10 milliliters of 50% sodamide in xylene whereupon the mixture was refluxed for one hour. After cooling 12 grams of 1-(2-benzyloxyethyl)-4-(3-chloropropyl)-piperazine were added and the mixture refluxed for four hours. The mixture was poured into water, extracted with ether, the ether phase washed with water and dried over anhydrous magnesium sulphate. The ether was evaporated, the residue dissolved in 96% ethanol and hydrogen chloride added. The precipitate was filltered off and consisted of 5 grams of the hydrochloride of 1-(2-benzyloxyethyl)-4-(3-chloropropyl)-piperazine. The filtrate was evaporated and the residue crystallized from acetone. 2.2 grams of the dihydrochloride of 2-trifluoromethyl-7-fluoro-10-(3-(4-(2-benzyloxyethyl) piperazine-1-yl)propyl)-phenothiazine were obtained as white crystals which melts at 200°–210° Centigrade.

The 2.2 grams of substance melting at 200°–210° Centigrade were heated on a steam bath with 25 milliliters of concentrated hydrochloric acid for 5 hours. The mixture was cooled, made alkaline with concentrated sodium hydroxide solution, extracted with ether. The ether phase was then washed and dried over anhydrous magnesium sulphate, and the dioxalate of 2-trifluoromethyl-7-fluoro-10-(3'-(4-(2-hydroxyethyl)-piperazine-1-yl)propyl)-phenothiazine precipitated by adding oxalic acid. The precipitate was filtered off and recrystallized from 350 milliliters of methanol. Yield: 1.1 grams. MP 218°–220° Centigrade.

The corresponding dihydrochloride melts at 218°–221° Centigrade.

EXAMPLE 2

2-Dimethylsulfamoyl-7-fluoro-10-(3-(4-methylpiperazin-1-yl)propyl)-phenothiazine and its dimaleate.

The starting material, N,N-dimethyl-7-fluorophenothiazine-2-sulphonamide, was prepared in the following way:

325 grams of 2-bromo-5-fluoroaniline were dissolved in 300 milliliters of concentrated hydrochloride acid (d = 1.2 grams/ml) and 350 milliliters of water. The mixture was heated to 60° Centigrade and cooled again to 0° Centigrade, whereupon 130 grams of sodium nitrite dissolved in 330 milliliters of water were added dropwise while the temperature was kept below 4° Centigrade. The reaction mixture was then left standing for 30 minutes while stirring and keeping the temperature at 0° centigrade. Then the mixture containing the diazonium compound formed was added at 60° Centigrade to a solution of 330 grams of potassium ethylxanthate in 400 milliliters of water. CAUTION ! At temperature below 60° Centigrade there may be risk of violent explosions due to accumulation of a diazoxanthate. After the addition has been completed the mixture was stirred for 30 minutes at 60° Centigrade, cooled and extracted with ether. The ether phase was separated and washed successively with 2N sodium hydroxide solution and water and evaporated. The residue was dissolved in 1 liter of 96% ethanol, and 400 grams of potassium hydroxide were added cautiously under reflux, whereupon the reaction mixture was refluxed for 18 hours. Water was added and the ethanol evaporated. 600 milliliters of concentrated hydrochloric acid and 50 grams of zink were added and the mixture steam distilled. The distillate was extracted with ether, the ether phase separated, washed with water, dried over anhydrous magnesium sulphate and evaporated. The residue was distilled at 35 mm Hg, whereby 160 grams of 2-bromo-5-fluorothiophenol boiling at 112°–116° Centigrade was obtained.

A mixture of 157 grams of 4-chloro-N,N-dimethyl-3-nitrobenzenesulphonamide, 116 grams of 2-bromo-5-fluorothiophenol, 24,4 grams of sodium hydroxide, 50 milliliters of water and 1.8 liters of 99% ethanol was refluxed for 30 minutes. The mixture was then evaporated and the residue poured on to crushed ice. The precipitate was sucked off and dried. Yield: 200 grams of N,N-dimethyl-4-(5-fluoro-2-bromophenylthio)-3-nitro-benzenesulphonamide which melts at 164°–166° Centigrade.

185 grams of N,N-dimethyl-4-(5-fluoro-2-bromophenylthio)-3-nitro-benzenesulphonamide dissolved in 3.5 liters of 50% ethanol were reduced with 25.5 milliliters of concentrated hydrochloric acid and 185 grams of iron dust by refluxing of the mixture for five hours. The mixture was cooled and filtered. The precipitate was dissolved in benzene, the benzene solution washed, dried over anhydrous magnesium sulphate and the benzene evaporated. The residue was recrystallized from methanol and 53.3 grams of N,N-dimethyl-7-fluoro-phenothiazine-2-sulphonamide obtained as white crystals which melts at 182°–184° Centigrade.

12 grams of N,N-dimethyl-7-fluoro-phenothiazine-2-sulphonamide were dissolved in 50 milliliters of dry dimethylformamide, 1.9 grams of 50% sodium hydride in oil added and the mixture stirred for 1 hour. 7.2 grams of 1-(3-chloropropyl)-4-methylpiperazine were then added and the mixture heated for two hours on a steam bath. Then the mixture was poured onto crushed ice, the resulting mixture extracted with ether, the ether phase washed, dried over anhydrous magnesium sulphate and the ether evaporated. 13 grams of 2-dimethylsulphamoyl-7-fluoro-10-(3-(4-methylpiperazin-1-yl)propyl)phenothiazine was thus obtained as a yellow oil. The dimaleate was made from an ethanol solution of the base and melted at 166°–169° Centigrade.

EXAMPLE 3

2-chloro-7-fluoro-10-(3-(4-(2-hydroxyethyl)piperazin-1-yl)propyl)-phenothiazine and its dihydrochloride.

The starting material, 2-chloro-7-fluorophenothiazine, was obtained in the following way:

A mixture of 250 grams of m-chloroacet-anilide, 500 grams of p-fluorobrombenzene, 80 grams of dry potassium carbonate, 5 grams of Adams Copper catalyst and 1 gram of cupro iodide was heated under reflux for 36 hours. After cooling the mixture was dissolved in acetone, filtered and evaporated. The residue was dissolved in a mixture of 600 milliliters of ethanol and 600 milliliters of concentrated hydrochloric acid and heated under reflux for 4 hours. The mixture was cooled, poured onto ice, extracted with ether, the ether phase washed with dilute aqueous ammonia, dried over anhydrous potassium carbonate, filtered and evaporated. The residue was distilled in vacuo and 200 grams of p-fluoro-m'-chlorodiphenyl amine obtained as a yellow oil boiling at 130°–135° Centigrade / 0.2 mm Hg.

150 grams of p-fluoro-m'-chlorodiphenylamine were mixed with 40 grams of sulphur and 4 grams of iodine and the mixture heated at 169° Centigrade for 1.5 hours. After cooling the mixture was extracted thoroughly with ether, the ether extracts filtered and the ether evaporated until crystallization began. 90 grams of 2-chloro-7-flurophenothiazine was obtained as a yellow crystalline substance which melts at 196° Centigrade.

To a solution of sodamide (from 3 grams of sodium) in 300 milliliters of ammonia were added 25 grams of 2-chloro-7-fluorophenothiazine, whereupon the mixture was stirred for one hour. 40 grams of 1-bromo-3-chloropropane were then added slowly, whereupon the ammonia was evaporated. Water was then added and the mixture extracted with ether, the etherphase dried over anhydrous potassium carbonate, filtered and evaporated. Excess of the bromochloropropane was removed by heating for half an hour on a steam bath at reduced pressure (1 mm Hg). To the residue were added 40 grams of N-(2-hydroxyethyl)-piperazine and the mixture heated for 18 hours on a steam bath. 500 milliliters of water were then added and the mixture extracted with ether. The etherphase was extracted with dilute hydrochloric acid, the acid aqueous phase made alkaline with sodium hydroxide and extracted with ether. The ether phase was dried over anhydrous potassium carbonate, filtered and evaporated. The residue was dissolved in 100 milliliters of ethanol and a solution of dry hydrogen chloride in ether added to pH 4. The crystalline precipitate was sucked off, washed with ether and dried. 15 grams of the dihydrochloride of 2-chloro-7-fluoro-10-(3-(4-(2-hydroxyethyl)piperazin-1-yl)propyl)-phenothiazine which melts at 225°–230° Centigrade were obtained.

EXAMPLE 4

2-Acetyl-7-fluoro-10-(3-(4-(2-hydroxyethyl)piperazin-1-yl)propyl)phenothiazine, its oxalate and maleate.

The starting material, 2-acetyl-7-fluorophenothiazine, was prepared in the following way:

108 grams of 3-fluorophenothiazine were dissolved in 1 liter of dry benzene. 75 grams of acetyl chloride were then added and the mixture heated under reflux for 4 hours, whereupon the mixture was evaporated. The residue was recrystallized from ethanol and 111 grams of 10-acetyl-3-fluorophenothiazine were obtained. MP: 125° Centigrade. The 111 grams of 10-acetyl-3-fluorophenothiazine were heated under reflux for 2 hours with 160 grams of anhydrous aluminium chloride in 800 milliliters of carbon disulphide. The mixture was cooled, and 70 grams of acetyl chloride were added slowly, whereupon the mixture was heated under reflux for 4 hours. The mixture was poured onto crushed ice and extracted with ether. The ether phase was evaporated, the residue dissolved in a mixture of 2 liters of ethanol and 50 milliliters of 50% sodium hydroxide solution and heated for 5 minutes on a steam bath. Thereby 2-acetyl-7-fluorophenothiazine crystallized out as white crystals which melt at 210° Centigrade. Yield: 80 grams.

By substituting 2-acetyl-7-fluorophenothiazine for 2-chloro-7-fluorophenothiazine in Example 3 and using a solution of oxalic acid in ether instead of a solution of hydrogen chloride in ether, the dioxalate of 2-acetyl-7-fluoro-10-(3-(4-(2-hydroxyethyl)piperazin-1-yl)propyl)phenothiazine was obtained as white crystals which melt at 212°–215° Centigrade. In corresponding manner was obtained the dimaleate which melts at 175 degrees Centigrade.

EXAMPLE 5

2-Chloro-7-fluoro-10-(3-dimethylaminopropyl)phenothiazine and its hydrochloride.

When example 3 was carried out and using heating with excess dimethylamine in an autoclave instead of heating with N-(2-hydroxyethyl)-piperazine, the hydrochloride of 2-chloro-7-fluoro-10-(3-dimethylaminopropyl)phenothiazine was obtained as white crystals which melt at 206°–207° Centigrade. Yield: 10 grams.

EXAMPLE 6

2-Trifluoromethyl-7-fluoro-10-(3-dimethylaminopropyl)phenothiazine and its oxalate When example 1 was carried out using 3-dimethylaminopropyl chloride instead of 1-(2-benzyloxyethyl)-4-(3-chloropropyl)-piperazine, the oxalate of 2-trifluoromethyl-7-fluoro-10-(3-dimethylaminopropyl)phenothiazine was obtained as white crystals which melt at 200°–201° Centigrade.

EXAMPLE 7

The palmitic acid ester of 2-trifluoromethyl-7-fluoro-10-(3'-(4-(2-hydroxyethyl)-piperazin-1-yl) propy)phenothiazine 10 grams of 2-trifluoromethyl-7-fluoro-10-(3'-(4-(2-hydroxyethyl)-piperazin-1-yl)propyl)phenothiazine were dissolved in 50 milliliters of chloroform. 8 grams of palmitoyl chloride were added and the mixture heated under reflux for one hour and evaporated in vacuum. The residue was dissolved in ether and washed with ice-water and then with a 10% sodium carbonate solution. The ether phase was separated, dried over anhydrous potassium carbonate, filtered and evaporated. The residue was extracted with petroleum ether and the petroleum ether extract evaporated to a small volume. Upon standing at 0° Centigrade the palmitic acid ester of 2-trifluoromethyl-7-fluoro-10-(3'-(4-(2-hydroxyethyl)-piperazin-1-yl)propyl) phenothiazine separates as a yellow crystalline substance which melts at 45°–50° Centigrade. Yield: 11 grams.

EXAMPLE 8

2-Trifluoromethyl-7-fluoro-10-(3'-(4-(2-hydroxyethyl)-piperazin-1-yl)propyl)phenothiazine-N-oxide and its oxalate 5 grams of 2-trifluoromethyl-7-fluoro-10-(3'-(4-(2-hydroxyethyl)-piperazin-1-yl)propyl)phenothiazine were dissolved in 50 milliliters of ethanol. 1.4 milliliter of 30% hydrogen peroxide were added and the mixture heated under reflux for 3½ hours. After cooling 0.2 grams of 10% palladium on carbon were added, and the mixture was heated on a steam bath for 5 minutes and filtered. After evaporation in vacuum and washing of the residue with ether the N-oxide was obtained as a yellow oil.

When dissolving the oil in ethanol and adding a solution of oxalic acid in acetone the mono-oxalate of 2-trifluoromethyl-7-fluoro-10-(3'-(4-(2-hydroxyethyl)piperazin-1-yl)propyl) phenothiazine-N-oxide was obtained as a white crystalline substance which melts at 190°–193° Centigrade. Yield: 3 grams.

EXAMPLE 9

2-trifluoromethyl-7-fluoro-10-(3'-(4-(2-hydroxyethyl)piperidine-1-yl)propyl)phenothiazine and its oxalate The starting material, 2-trifluoromethyl-7-fluoro-10-(3-chloropropyl)phenothiazine, was prepared in the following way:

8.5 grams of 2-trifluoromethyl-7-fluoro-phenothiazine were added to 3.1 grams of sodamide in 200 milliliters of liquid ammonia and the mixture stirred for half an hour. Then 10 grams of 3-bromo-1-chloropropane and 10 milliliters of dry toluene were added, followed 15 minutes later by further 50 milliliters of dry toluene. The mixture was stirred for one hour, whereupon the mixture was evaporated on a steam bath. The residue was dissolved in 400 milliliters of ether, the ether solution washed three times with water (100 milliliters each time), dried over anhydrous magnesium sulphate and evaporated in vacuum. 10 grams of 2-trifluoromethyl-7-fluoro-10-(3-chloropropyl) were thus obtained as a yellow oil.

40 grams of 4-(2-hydroxyethyl)piperidine were then added, and the mixture heated for 17 hours at 90° Centigrade. The mixture was cooled, poured into water, extracted with 500 milliliters of ether, the ether extract washed five times with water and dried over anhydrous magnesium sulphate. The oxalate of 2-trifluoromethyl-7-fluoro-10-(3'-(4-(2-hydroxyethyl)-piperidin-1-yl)propyl)phenothiazine was precipitated from acetone-/ether (1:1) and melts at 76°–80° Centigrade. The pharmacological testing of the compounds of the present invention consisted of a standard and reliable, published test showing the neuroleptic activity of the compounds in that they antagonize central nervous stimulating compounds such as amphetamine and methylphenidate. The methylphenidate test was selected after it had proved to be a reliable test method on several known neuroleptics and reference is made to Pedersen, V. & Christensen, A.V.: "Methylphenidate antagonism in mice as a rapid screening test for neuroleptic drugs." Acta pharmacol. et toxicol. 1971, 29, suppl. 4, 44.

The test may briefly be described as follows:

As animals were used NMRI male mice weighing 18–25 grams. 3 × 2 mice are used for each dose level.

2, 6 or 24 hours after i.p.injection of test substance, methylphenidate, 60 mg/kg, is injected s.c. After administration of methylphenidate the mice are placed in the observation cages, 2 in each cage, where they remain for 2, 6 or 24 hours. The cages are placed on corrugated paper, the corrugations facing upwards. It is examined whether or not the mice have been biting the corrugated paper. If not, the substance has had an antagonistic effect. If one or more of the control pairs have also not been biting the corrugated paper, the test has to be repeated on a new set of mice. The following novel substances of Formula I were tested:

2-trifluoromethyl-7-fluoro-10-(3'-(4-(2-hydroxyethyl)-piperazine-1-yl)propyl)phenothiazine (Lu 10-116),
2-chloro-7-fluoro-10-(3'-(4-(2-hydroxyethyl)-1-piperazinyl)propyl)-phenothiazine (Lu 10-125),
2-dimethylsulfamoyl-7-fluoro-10-(3'-(4-methyl-piperazin-1-yl)-propyl)phenothiazine (Lu 11-075),
2-acetyl-7-fluoro-10-(3'-(4-(2-hydroxyethyl)-1-piperazinyl)-propyl)phenothiazine (Lu 11-087) and
2-chloro-7-fluoro-10-(3'-dimethylaminopropyl)-phenothiazine (Lu 10-152).

As reference substances were used the corresponding known phenothiazines having no fluorine substitution at position 7, namely fluphenazine, perphenazine, thioproperazine, acetophenazine and chlorpromazine respectively.

The results will appear from the following table:

| Substance No. | Methylphenidate Antagonism $ED_{50}$ mg/kg i.p. | | |
|---|---|---|---|
| | 2h | 6h | 24h |
| Lu 10-116 | 0.11 | 0.01 | 0.08 |
| Lu 10-125 | 0.06 | 0.05 | >5 |
| Lu 11-075 | 0.70 | 0.44 | >5 |
| Lu 11-087 | 0.06 | 0.07 | >1.25 |
| Lu 10-152 | 2.0 | 2.1 | >20 |
| Fluphenazine | 0.08 | 0.03 | >2.5 |
| Perphenazine | 0.08 | 0.55 | >5 |
| Thioproperazine | 0.28 | 1.2 | >5 |
| Acetophenazine | 0.20 | 4.4 | >10 |
| Chlorpromazine | 3.3 | >20 | >20 |

From the table it appears that the most active compound of those tested has a peak effect about 6 hours after administration but, even after 24 hours there is still a very strong effect.

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection.

Results upon administration to human beings have been very gratifying.

Most conveniently, the compounds of Formula I are administered orally in unit dosage form such as tablets or capsules, each dosage unit containing a non-toxic acid addition salt of one of the said compounds in an amount of from about 0.1 to about 50 mg, most preferably, however, from about 0.5 to 25 mg, calculated as the free amine, the total daily dosage usually ranging from about 0.5 to about 300 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

Typical examples of formulas for compositions containing 2-trifluoromethyl-7-fluoro-10-(3'-(4-(2-hydroxyethyl)-piperazine-1-yl)propyl)phenothiazine (called Lu 10-116 for short) as the active ingredient are as follows:

1. Tablets containing 1 milligram of Lu 10-116 calculated as the free base in the form of the dioxalate:

| | |
|---|---|
| Lu 10-116 | 1 mg |
| Lactose | 37 mg |
| Potato starch | 74 mg |
| Gelatine | 2 mg |
| Talcum | 8 mg |

2. Solutions for injection containing per ml:

| | |
|---|---|
| Lu 10-116 | 0.5 mg |
| Sodium chloride | 9.0 mg |
| Sterile water | ad 1 ml |

3. Syrup containing per milliliter:

| | |
|---|---|
| Lu 10-116 | 0.2 mg |
| Methyl-paraben | 1.0 mg |
| Propyl-paraben | 0.1 mg |
| Saccharose | 400 mg |
| Water | ad 1 ml |

4. Capsules containing per capsule:

| | |
|---|---|
| Lu 10-116 | 2 mg |
| Lactose | 40 mg |
| Magnesium stearate | 0.5 mg |

Any other pharmaceutical tableting adjuvants may be used provided that they are compatible with the active ingredient, and additional compositions and dosage forms may be similar to those presently used for neuroleptics such as fluphenazine, perphenazine or thioproperazine. Also combination of the compounds of Formula I as well as their non-toxic acid salts with other active ingredients especially other neuroleptics, thymoleptics, tranquilizers, or the like, fall within the scope of the present invention.

As previously stated, when isolating the compounds of Formula I in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, embonates and maleates of the amines of Formula I. Other acids are likewise suitable and may be employed if desired. For example, fumaric, benzoic, ascorbic, succinic, salicylic, bismethylenesalicylic propionic, gluconic, malic, malonic, madelic, cinnamic, citraconic, stearic, palmitic, itaconic, glycolic, benzenesulphonic, and sulphamic acids may also be employed as acid addition saltforming acids. When it is desired to isolate a compound of the invention in the form of the free base, this may be done according to conventional procedure, as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals by administering to a living animal body, including human beings an adequate quantity of a compound of Formula I or a non-toxic acid addition salt thereof. An adequate quantity would be from about 0.001 mg to about 1 mg per kg of body weight in each unit dosage and from about 0.003 milligrams to about 3 milligrams/kg of body weight per day.

We claim:
1. A compound selected from the group consisting of 1) a 7-fluoro substituted phenothiazine of the formula:

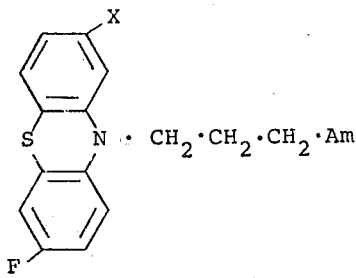

wherein "Am" is selected from the group consisting of $N(CH_3)_2$ and

X is selected from the group consisting of —Cl, —$CF_3$, —$CO \cdot CH_3$ and —$SO_2 \cdot N(CH_3)_2$, Y is selected from the group consisting of >NH, >$N \cdot CH_3$, >$N \cdot CH_2 \cdot CH_2OH$, >$N \cdot CH_2 \cdot CH_2OAc$  >$CH \cdot CH_2 \cdot CH_2OH$ and >$CH \cdot CH_2 \cdot CH_2OAc$, and —Ac is an acyl radical of an aliphatic carboxylic acid having one to seventeen carbon atoms inclusive, 2) a N-oxide thereof, and 3) an acid addition salt thereof with a pharmaceutically acceptable acid.

2. A compound according to claim 1, characterized thereby that X is —$CF_3$ and "Am" is

wherein Y is selected from the group consisting of >NH, >$N \cdot CH_3$, >$N \cdot CH_2 \cdot CH_2OH$, >$N \cdot CH_2 \cdot CH_2OAc$, >$CH \cdot CH_2 \cdot CH_2OH$ and >$CH \cdot CH_2 \cdot CH_2OAc$, wherein —Ac is an acyl radical of an aliphatic acrboxylic acid having one to seventeen carbon atoms inclusive, a N-oxide thereof, and an acid addition salt thereof with a pharmaceutically acceptable acid.

3. A compound according to claim 1 or 2, characterized thereby that X is —$CF_3$ and "Am" is

wherein Y is selected from the group consisting of $N \cdot CH_2 \cdot CH_2OH$ and >$N \cdot CH_2 \cdot CH_2 \cdot CH_2OAc$, wherein —Ac is an acyl radical of an aliphatic carboxylic acid having one to seventeen carbon atoms inclusive, a N oxide thereof, and an acid additions salt thereof with pharmaceutically acceptable acid.

4. 2-Trifluoromethyl-7-fluoro-10-(3'-(4-(2-hydroxyethyl)-piperazin-1-yl(propyl)phenothiazine and acid addition salts thereof with pharmaceutically acceptable acids.

5. 2-Trifluoromethyl-7-fluoro-10-(3'-(4-(2-hydroxyethyl)-piperazin-1-yl)propyl)phenothiazine dihydrochloride.

6. 2-Trifluoromethyl-7-fluoro-10-(3'-(4-(2-hydroxyethyl)-piperazin-1-yl)propyl)phenothiazine.

7. 2-Dimethylsulfamoyl-7-fluoro-10-(3'-(4-methylpiperazin-1-yl)propyl)phenothiazine and acid addition salts thereof with pharmaceutically acceptable acids.

8. 2-Dimethylsulfamoyl-7-fluoro-10-(3'-(4-methylpiperazin-1-yl)propyl)phenothiazine dimaleate.

9. 2-Chloro-7-fluoro-10-(3'-(4-(2-hydroxyethyl)piperazin-1-yl) propyl)phenothiazine and acid addition salts thereof with pharmaceutically acceptable acids.

10. 2-Chloro-7-fluoro-10-(3'-(4-(2-hydroxyethyl)-piperazine-1-yl) propyl)phenothiazine dihydrochloride.

11. 2-Chloro-7-fluoro-10-(3'-(4-(2-hydroxyethyl)-piperazin-1-yl) propyl)phenothiazine.

12. 2-Acetyl-7-fluoro-10-(3'-(4-(2-hydroxyethyl)-piperazin-1-yl) propyl)phenothiazine and acid addition salts thereof with pharmaceutically acceptable acids.

13. 2-Acetyl-7-fluoro-10-(3'-(4-(2hydroxyethyl)piperazin-1-yl) propyl)phenothiazine dimaleate.

14. 2-Acetyl-7-fluoro-10-(3'-(4-(2-hydroxymethyl)-piperazine-1-yl) propyl)phenothiazin.

15. The palmitic acid ester of 2-trifluoromethyl-7-fluoro-10-(3'-(4-(2-hydroxyethyl)piperazin-1-yl)propyl)phenothiazine.

16. A compound of the formula:

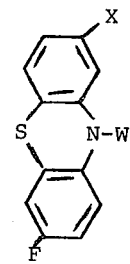

wherein
W and X are defined as follows:

X is selected from the group consisting of —Cl, —CF$_3$, —CO·CH$_3$ and —SO$_2$·N(CH$_3$)$_2$, and W is selected from the group consisting of a hydrogen atom and a group —CH$_2$·CH$_2$·CH$_2$—Z, wherein Z represents an electronegative radical selected froom the group consisting of chlorine, bromine, methylsulphate, toluene-p-sulphonate, and methanesulphonate.

17. A compound of the formula:

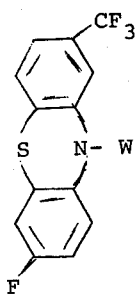

wherein
W is defined as follows:
W is selected from the group consisting of a hydrogen atom and a group —CH$_2$·CH$_2$·CH$_2$—Z, wherein Z represents an electro-negative radical selected from the group consisting of chlorine, bromine, methylsulphate, toluene-p-sulphonate, and methanesulphonate.

18. A pharmaceutical composition in unit dosage form comprising a major quantity of a pharmaceutically-acceptable carrier and a pharmaceutically effective dose of a compound as defined in claim 1.

19. A composition according to claim 18, comprising the pharmaceutically-acceptable carrier and wherein the active ingredient is present in an amount of from 0.01 mg to 100 mg per unit dose calculated as the free amine.

20. A composition according to claim 18, comprising the pharmaceutically-acceptable carrier and wherein the active ingredient is 2-trifluoromethyl-7-fluoro-10-(3'-94-(2-hydroxyethyl)piperazin-1-yl)propyl)phenothiazine or a pharmaceutically-acceptable acid addition salt thereof.

21. A method for the treatment of psychotic disorders in a living animal subject in need of such treatment, comprising the step of administering to the said subject in need of such treatment a neuroleptically-effective amount of a compound as defined in claim 1.

22. The method of claim 21, wherein the neuroleptically-active compound is administered in an amount of from 0.01 mg to 100 mg per unit dose, calculated as the free amine.

23. The method of claim 21, wherein the neuroleptically-active compound is 2-trifluoromethyl-7-fluoro-10-(3'-(4-(2-hydroxyethyl)piperazin-1-yl)propyl)-phenothiazine or a pharmaceutically-acceptable acid addition salt thereof.

24. The method of claim 21, wherein the neuroleptically-active compound is administered in an amount of about 0.001 mg to 1 mg per kilogram of body weight per unit dose.

25. The method of claim 21, wherein the neuroleptically-active compound is administered in an amount of about 0.003 mg to about 3 mg per kilogram of body weight per day.

* * * * *

UNITED STATES PATENT OFFICE
CERTIFICATE OF CORRECTION

Patent No. 3,966,930          Dated June 29, 1976

Inventor(s) Jorn Lasse Martin Buus and Niels Lassen

It is certified that error appears in the above-identified patent and that said Letters Patent are hereby corrected as shown below:

| | should read: |
|---|---|
| Col. 4, Line 22:<br>"64°-64°" | --- 64°-65° --- |
| Col. 4, Line 65:<br>"erazine-1-yl)" | --- erazin-1-yl) --- |
| Col. 7, Line 63:<br>"propy)phenothiazine" | --- propyl)phenothiazine --- |
| Col. 12, Line 39:<br>"piperazine-1-yl)" | --- piperazin-1-yl) --- |
| Col. 12, Line 46:<br>"(2hydroxyethyl)" | --- (2-hydroxyethyl) --- |
| Col. 12, Line 48:<br>"(2-hydroxymethyl)" | --- (2-hydroxyethyl) --- |
| Col. 13, Line 6:<br>"froom" | --- from --- |
| Col. 14, Line 9:<br>"(3'-94-" | --- (3'-(4- --- |

Signed and Sealed this

Ninth Day of November 1976

[SEAL]

Attest:

RUTH C. MASON
Attesting Officer

C. MARSHALL DANN
Commissioner of Patents and Trademarks